United States Patent
Hsu

(10) Patent No.: US 6,197,815 B1
(45) Date of Patent: *Mar. 6, 2001

(54) AMINO ACID CHELATES TO REDUCE STILL BIRTHS AND INCREASE BIRTH WEIGHT IN NON-HUMAN ANIMALS

(75) Inventor: Hsinhung John Hsu, Ventura, CA (US)

(73) Assignee: J.H. Biotech, Inc., Ventura, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/040,862

(22) Filed: Mar. 18, 1998

(51) Int. Cl.$^7$ ............ A16K 33/24; A16K 33/26; A16K 33/20; A16K 33/32; A16K 33/34; A16K 33/42; A16K 3/28; A16K 3/295; A16K 33/00; A16K 33/04; A16K 33/06; A16K 33/14; A16K 33/22

(52) U.S. Cl. ............ 514/502; 424/696; 424/697; 424/709; 424/715; 424/718; 424/722; 424/DIG. 6; 424/601; 424/602; 424/603; 424/604; 424/605; 424/606; 424/617; 424/630; 424/631; 424/632; 424/633; 424/634; 424/635; 424/637; 424/638; 424/639; 424/640; 424/641; 424/643; 424/646; 424/647; 424/648; 424/655; 424/657; 424/658; 424/659; 424/660; 424/663; 424/681; 424/682; 424/683; 424/686; 424/687; 424/688; 424/689; 424/692; 424/693; 514/400; 514/419; 514/423; 514/452; 514/462; 514/471; 514/492; 514/494; 514/499; 514/500; 514/501; 514/505; 514/556; 514/557; 514/561; 514/562; 514/564; 514/565; 514/567; 514/574; 514/814; 514/836; 426/807

(58) Field of Search .................. 514/492, 494, 514/499, 501, 502, 561, 574, 400, 419, 423, 556, 557, 562, 564–565, 567, 452, 462, 471, 500, 505, 814, 836; 424/601–606, 617, 630–635, 637–641, 643, 646–648, 655, 657–660, 663, 681–683, 686–689, 692–693, 696–697, 709, 715, 718, 722, DIG. 6; 426/807

(56) References Cited

U.S. PATENT DOCUMENTS

| | | | |
|---|---|---|---|
| 3,975,513 | 8/1976 | Hecht et al. | 424/482 |
| 3,991,750 | 11/1976 | Vickery | 424/425 |
| 4,183,947 | * 1/1980 | Cockerill | 514/502 |
| 4,191,741 | 3/1980 | Hudson et al. | 424/425 |
| 4,220,153 | 9/1980 | Dresback | 424/438 |
| 4,326,523 | 4/1982 | Wolfrom et al. | 424/426 |
| 4,599,152 | 7/1986 | Ashmead | 205/435 |
| 4,830,716 | 5/1989 | Ashmead | 205/435 |
| 4,863,898 | 9/1989 | Ashmead | 514/6 |
| 5,504,055 | * 4/1996 | Hsu | 504/121 |

OTHER PUBLICATIONS

Rao, K.S. et al., "In Vitro Studies on Chelating Agents as Potential Iron Absorption Promoters," Food Chemistry, vol. 17, pp. 13–23, 1985.*

Chemical Abstracts 100:155531f, 1984.*

Chemical Abstracts 101:89380y, 1984.*

* cited by examiner

Primary Examiner—John Pak
(74) Attorney, Agent, or Firm—Koppel & Jacobs; Michael J. Ram

(57) ABSTRACT

Metal amino acid chelates for animals are beneficial for facilitating and promoting growth by increasing desired metallic ion uptake. The present invention is directed to a process for providing an animal fed additive by preparing metal amino acid chelates, and the metal amino acid chelate growth facilitator, promoter and enhancer prepared by the process.

20 Claims, No Drawings

AMINO ACID CHELATES TO REDUCE STILL BIRTHS AND INCREASE BIRTH WEIGHT IN NON-HUMAN ANIMALS

BACKGROUND OF THE INVENTION

1. Area of the Art

The present invention relates to amino acid chelates and methods of supplying animals with desired nutrients. Particularly, the present invention relates to the use of metal amino acid chelates to facilitate and promote the growth of animals. Expressly incorporated herein by reference is applicant's U.S. Pat. No. 5,504,055, for METAL AMINO ACID CHELATE, which issued on Apr. 2, 1996.

2. Description of the Prior Art

Stable amino acid chelates are capable of imparting nutritional benefits to living systems. Owing to more expedient and efficient assimilation, chelated forms of metals have become known to create desired levels of certain metals in living systems including, for example, plants. Others have developed processes for chelating which have attempted to react metal salts with amino acids, and resulting products have had solubility, pH and stability constraints.

It has thus become generally accepted that the chelated forms of these metals with amino acids are demonstrably better assimilated by plants, animals, and human beings than metal salts, the plant, animal and human tissues showing increased metal content when exposed to metal amino acid chelates. Prior art metal amino acid chelates are formed by reacting metal salts with amino acids. For example, metal salts, such as salts of iron, zinc, copper, magnesium, cobalt or calcium, when reacted with an amino acid, for example glycine, would form ferrous glycinate, zinc glycinate, copper glycinate, magnesium glycinate, cobalt glycinate, cobalt glycinate, or calcium glycinate, respectively.

Likewise, the metal amino acid chelates made according to the prior art processes result in products that are insoluble or unstable in water, particularly at a low pH or a pH above 7 As fully discussed in applicant's aforementioned U.S. Pat. No. 5,504,055, which has been expressly incorporated herein by reference, the chelation process shown in certain prior art references required heating under nitrogen (For example, per U.S. Pat. Nos. 2,877,253 and 2,957,806). Other prior art techniques produced chelates which were unstable or precipitated at a pH above 8 (U. S. Pat. Nos. 4,216,143 and 4,216,144).

Additionally, these prior art chelates have been known to precipitate out of solution when other chemical compounds, such as phosphates, are added to the chelate solution.

Prior art chelates also show stability problems over a period of time, the compounds precipitating after two or three days (U.S. Pat. No. 4,216,144). U.S. Pat. No. 3,396,104 shows formation of insoluble metal proteinates using saline water.

Likewise, there exists a longstanding desire to promoting animal growth, and various attempts to accomplish the same have employed elaborate and circumlocuted means. It has now been discovered that enhanced metal amino acid chelates incorporating features of the invention promotes growth in animals.

The present inventor has overcome significant aspects of both of these problems by developing, and patenting a material capable of delivering high levels of desired metal ions to agricultural products. Other attempts to address the clear need for supplying animals with selected compounds over time have taken different and convoluted paths, from subcutaneous implants to complex salts having cations being made from complexes including iron and methionine. However, nothing among the prior art has adequately addressed increasing desired metal uptake by the animal, and concomitant growth facilitation and enhancement for the treated animals.

By way of example, U.S. Pat. No. 3,991,750; which issued Nov. 16, 1976 to Vickery, and is assigned to SYNTEX CORPORATION, disclosed implantation of dromostanolone propionate subcutaneously to produce weight gain, inter alia. Without precisely elucidating the mechanism, the disclosure suggests that bioavailability of iron and methionine is effective for this purpose. Likewise, according to the process of the present invention, use of metal amino acid chelates demonstrably enhanced piglets, and juvenile chickens. However, no need for radical or surgical invasion is present in accordance with the instant teachings.

U.S. Pat. No. 4,067,994; which issued Jan. 10, 1976 to Anderson et al., and is assigned to ZINPRO CORP., likewise pointed to the use of novel complexers as food additive for enhancing growth. However, as mentioned above, and discussed in detail below, the use of salts for nutritional supplementation substantially constrains the utility of the involved compounds in terms of solubility, stability and pH. Further, problems with precipitating out of solution and the like degrading mechanisms abound when using salts.

U.S. Pat. No. 4,326,523; which issued Apr. 27, 1982 to Wolfrom et al., and is assigned to INTERNATIONAL MINERAL & CHEMICAL CORP., also disclosed an implanted means for administering compounds including metals, over time to animals. In contradistinction to the instant teachings, this elaborate means for introduction likewise adds difficulty and militates strongly for the need for applicant' novel method for enhancing and facilitating the growth of livestock.

OBJECTS AND SUMMARY OF THE INVENTION

Accordingly, it is a prime objective of the present invention to provide a process for preparing metal amino acid chelates beneficial to animal growth which overcome the drawbacks of the prior art.

It is another object of the present invention to provide a process for promoting animal growth by the use of amino acid chelates having demonstrable results and benefits.

It is yet another object of the present invention to provide the above objects in a process for producing a metal complex and offering the same for consumption to animals, whereby mortality is decreased and weight and feed conversion parameters are enhanced.

Briefly stated, metal amino acid chelates administered in accordance with the invention to animals are beneficial for facilitating and promoting growth by increasing desired metallic ion uptake. The present invention is directed to a process for providing an animal feed additive by preparing unique metal amino acid chelates, and the metal amino acid chelate growth facilitator, promoter and enhancer prepared by the process.

Further, the present invention is directed to metal amino acid chelates which are soluble in water wherein the solution taught has a pH from about 4.5 to about 8.5. Still further the invention is directed to metal amino acid chelates which are stable over an extended period of time, the stability or solubility not being adversely effected by the addition of other additives to the solution.

The process for preparing metal amino acid chelates of the present invention comprises the production of a solution of the desired metal ion by dissolving a water soluble salt of the metal in deaerated water, adding the salt solution to an acid solution prepared by mixing an organic acid with an amino acid to form a chelate, and adjusting the pH of the solution to a pH between 4.5 and 8.5.

The process results in a chelate of the metal ion with the amino acid and the organic acid, the chelate having a unique composition as demonstrated by the spectral analysis According to a feature of the present invention, there is provided a process for facilitating and promoting growth in animals, comprising preparing a metal containing composition comprising the steps of deaerating water, dissolving a metal salt in the deaerated water to produce a salt solution, mixing an organic acid with an amino acid to provide an organic solution, forming a chelate solution by adding the organic solution to the salt solution and adjusting the pH of the chelate solution to a range of from about 4.5 to about 8.5 by the addition of a base solution to yield an enhanced chelate, combining an effective amount of said enhanced chelate with animal feed, and administering a resulting mixture to animals.

According to an additional feature of the present invention, there is provided a composition of matter for facilitating and promoting the growth of animals comprising an effective amount of at least one metal complex said at least one metal complex produced by blending a metal salt, an amino acid and an organic hydroxy acid in deaerated water, the composition of matter being substantially soluble at a pH from about 4.5 to about 8.5, said complex having the structure:

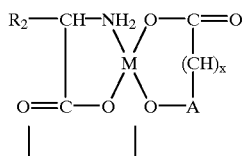

Where M = a metal ion,
x = 0 or 1, and A = —C═O or —CR₁R₃ wherein; $R_1$=the carbon chain from the organic hydroxy acid, on malonic acid which may be optionally substituted with —OH or —COOH, $R_2$=H, or the carbon chain radical from the α-position of the amino acid, and $R_3$=—H or —COOH.

The above, and other objects, features, advantages, and innovations of the present invention will become apparent from the following description, examples, experiments, tables, charts and data, in addition to the claims appended hereto defining the metes and bounds of the present invention and those equivalents under law which are at the ordinary skill level of one knowledgeable in the instant fields of art.

DETAILED DESCRIPTION OF THE INVENTION

The present inventor has discovered that a composition of matter comprising a metal complex produced by blending a metal salt, an amino acid and an organic hydroxy acid in deaerated water is effective for facilitating and promoting the growth of animals.

According to the process of the present invention, use of metal amino acid chelate for animals facilitates and promotes growth of the same. Exemplary, but not limitative, embodiments of applicant's enhanced chelate are demonstrative of ways of generating the metal composition which is combined with animal feed according to the teachings of the process of the present invention.

Water is deaerated by boiling for at least 30 minutes. A quantity of a water soluble salt of the desired metal ion is then added to the deaerated water with stirring, the solution being maintained at a temperature of at least about 80° C. An acid solution is also prepared by mixing an organic acid with an amino acid, the two acids being combined in a ratio of about 1:1 to about 1:10 respectively. The ratio of the two acids depends on the number of —NH₂, or —COOH groups in each compounds and/or the valence of the metal ion to be added. While not required, it is preferred that each solution is filtered prior to proceeding with the next step so that the mixtures do not include any undissolved material.

The metal salt solution and the acid solution are then combined with mixing so that the mole ratio of metal ion to acid is about 1:2, the mixture being maintained at 80° C. to produce a metal amino acid chelate solution. Undissolved material can then be filtered from the chelate solution and the chelate solution can be applied to animal feed. Alternatively, the chelate solution can be dried by standard processing techniques, the dried material converted to fine granules or powder and the resultant dry material packaged for later use. If the product is not used in its liquid state but instead is dried, the maximum drying temperature is preferred to be no greater than about 110° C. Higher temperatures tended to cause decomposition of the chelate.

The process of the invention is applicable to a broad range of metal ions including water soluble salts of iron, cobalt, copper, zinc, manganese, magnesium, calcium, chromium, boron, molybdenum, and nickel or mixtures thereof. A list of representative metal salts includes the water soluble carbonates, sulfates, nitrates, oxides, hydroxides, chlorides, phosphates and acetates or mixtures thereof.

A broad range of organic acids, including acids with more than one carboxyl groups and one or more hydroxyl groups, and amino acids have also been found to be usable in the process of the invention. Suitable organic acids include citric acid, malonic acid, tartaric acid, lactic acid and gluconic acid or mixtures thereof. Amino acids, with or without the addition of a broad range of substituents including, but not limited to a second carboxyl group (i.e., aspartic acid or glutamic acid), a carboxamide (i.e., asparagine), a second basic group such as an amino group (i.e., lysine), an guanidino group (i.e., arginine), an imidazole ring (i.e., histidine), a benzene or heterocyclic ring system, phenolic or alcoholic hydroxyl groups, halogen or sulfur atoms are suitable for the process of the invention. Preferred amino acids include glycine, lysine, methionine, cysteine, glutamic acid and aspartic acid and mixtures thereof. Increasing the pH up to about 8.5 does not affect the clear character of the solution.

The preferred base for adjusting the pH is potassium hydroxide which also resulted in a chelate with the potassium present. Sodium hydroxide is also suitable. Alternatively, uses of ammonium hydroxide results in a chelate with an increased nitrogen content. Thus, in addition to producing a chelate with an enhanced ability to deliver a metal ion to a treated animal, the use of these materials also allows the delivery of potassium, and/or nitrogen to the animal. These materials are also recognized as being beneficial to the production of healthy animals.

Highly critical to the invention is the deaeration of the water used to produce the chelate. The presence of dissolved oxygen appears detrimental to the end product as it can result in a shifting of the valence state of the metal (e.g., Fe+2 to Fe+3).

It is also important that the calcium and magnesium content of the water be reduced or eliminated. Suitable procedures include distillation, deionization or softening the water.

The metal amino acid chelate solution prepared according to the process of the invention had a mineral content in the range of 250 to 50,000 parts per million.

The chemical structure of the metal amino acid chelate is believed to be:

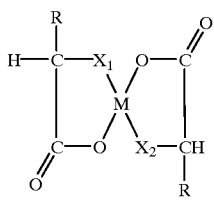

Where $X_1=NH_2$ and $X_2=NH_2$ or O. M is a metal ion and R a carbon containing compound derived from the amino acid or organic acid with or without the addition of —S, —$NH_2$, —COOH or other groups commonly making up amino acids or organic acids. There are two molecules of the chelating agent to 1 molecule of metal. A ring structure is formed between each of the chelating agents and the metal.

It is possible that organic acid may substitute for some of the amino acid groups. In this case, one of the chelating agent is amino acid and the other one is organic acid and at least one —X in the formula is —O and R represents constituents of common organic acids. This may increase the stability of the chelates.

In order to more clearly define the enhanced chelate aspects of the invention, the following examples of methods of preparation are set forth. These examples are illustrative only and are not limiting as to the scope of the invention. Examples I, II, III, IV, V, VI, VII, and VIII set forth processes embodying features of the invention relating to applicant's novel enhanced chelate as used according to the process for promoting growth of animals which is the subject matter of the instant application.

Likewise, a series of Experiments follow the examples, and the Experiments which follow the Examples demonstrate the superiority of the enhanced chelate prepared according to the process of the invention over the prior art methods of promoting the growth of animals.

EXAMPLE I
(iron/citrate/glycine chelate)

(1) 1,000 grams of water were placed in a beaker, heated to 100° C. followed by boiling for 30 minutes.

(2) 133 grams of ferrous carbonate monohydrate were added to the boiling water and the mixture was stirred constantly while keeping the temperature of the mixture at or above about 80° C.

(3) 30 grams of citric acid were mixed with 150 grams of glycine and then the acid mixture was add to the ferrous carbonate solution.

(4) The temperature of the mixture was maintained at or above about 80° C. with constant stirring until no more solid went into solution.

(5) The mixture was filtered to remove the undissolved materials and the filtrate was dried at a temperature not in excess of 110° C.

(6) The dry material, referred to as an iron amino acid chelate, is hereafter designated as Sample I.

EXAMPLE II
(iron/citrate/glycine chelate)

(1) 1,000 grams of water were boiled for 30 minutes to remove dissolved air.

(2) 170 grams of ferrous sulfate monohydrate were dissolved in the deaerated water and the solution was maintained at 80° C.

(3) 30 grams of citric acid were mixed with 150 grams of glycine and the acid solution was added to the ferrous sulfate solution with stirring. The temperature of the mixture was maintained at about 80° C. until no more solids would dissolve.

(4) The mixture was filtered to remove any undissolved materials, the filtrate was dried at about less than about 110° and the dry material was ground to a fine powder.

(5) The ground material, referred to as an iron amino acid chelate, is hereafter designated as Sample II.

EXAMPLE III
(calcium/malonic/lysine chelate)

(1) 1,000 grams of water were boiled for 30 minutes to remove dissolved air.

(2) After the water cooled, 100.1 grams of calcium carbonate were added to the deaerated water with constant stirring.

(3) 60 grams of malonic acid were mixed with 292.5 grams of lysine and then the acid mixture was added to the calcium carbonate solution.

(4) The mixture was stirred until no more material would dissolve, the mixture was filtered to remove the undissolved materials., and the filtrate was dried at less than about 110° C.

(5) The dry material was ground and labeled, and is hereafter designated as Sample III.

EXAMPLE IV
(calcium/malonic/lysine chelate)

(1) 1,000 grams of water were boiled for 30 minutes to remove dissolved air.

(2) After the water cooled, 111.0 grams of calcium chloride were added to the deaerated water with constant stirring.

(3) 60 grams of malonic acid were mixed with 292.5 grams of lysine and the acid solution was added to the calcium chloride solution.

(4) The mixture was stirred continuously until no more material would dissolve, the mixture was filtered to remove the undissolved materials, and the filtrate was dried at 110° C.

(5) The dry material was ground to a powder and, is hereafter designated as Sample IV.

EXAMPLE V
(copper/citrate/aspartic chelate)

(1) 1,000 grams of water were boiled for 30 minutes to remove air.

(2) After the water cooled, 97.6 grams of cupric hydroxide were added to the deaerated water with constant stirring.

(3) 30 grams of citric acid were mixed with 266.2 grams of aspartic acid and then the acid solution was added to the cupric hydroxide-water mixture.

(4) The mixture was held at about 80° C. and with constant stirring until no more material would dissolve and the mixture was passed through a filter to remove any undissolved materials.

(5) The filtrate was dried at less than about 110° C. to obtain a copper amino acid chelate.

EXAMPLE VI
(magnesium/citrate/glycine chelate)

(1) 1,000 grams of water were boiled for 30 minutes to remove air.

(2) After the water cooled, 24.3 grams of powdered magnesium metal were added to the deaerated water with constant stirring.

(3) 30 grams of citric acid were mixed with 150 grams of glycine and the acid solution was added to the magnesium-water mixture.

(4) The mixture was held at about 80° C. with continuous stirring until no more material would dissolve and the mixture was passed through a filter to remove the undissolved materials.

(5) The filtrate was dried at less than about 110° C. to obtain a magnesium amino acid chelate.

EXAMPLE VII
(zinc/citrate/glutamate chelate)

(1) 1,000 grams of water were boiled for 30 minutes to remove air.

(2) After the water cooled, 81.4 grams of zinc oxide were added to the deaerated water with constant stirring.

(3) 30 grams of citric acid were mixed with 294.2 grams of glutamic acid and then added to the zinc oxide-water mixture.

(4) The mixture was held at about 80° C. with continuous stirring until no more material would dissolve and the mixture was passed through a filter to remove the undissolved materials.

(5) The filtrate was dried at less than about 110° C. to obtain a zinc amino acid chelate.

EXAMPLE VIII
(manganese/citrate/methionine chelate)

(1) 1,000 grams of water were boiled for 30 minutes to remove air. (2) After the water cooled, 277.1 grams of manganous sulfate heptahydrate were added to the deaerated water with constant stirring.

(3) 30 grams of citric acid were mixed with 298.5 grams of methionine and then added to the manganous sulfate heptahydrate-water mixture.

(4) The mixture was held at about 80° C. with continuous stirring until no more material would dissolve and the mixture was passed through a filter to remove the undissolved materials.

(5) The filtrate was dried at less than about 110° C. to obtain a manganese amino acid chelate.

EXAMPLE IX
(cobalt/citrate/cysteine chelate)

(1) 1,000 grams of water were boiled for 30 minutes to remove air.

(2) After the water cooled, 118.9 grams of cobalt carbonate were added to the deaerated water with constant stirring.

(3) 30 grams of citric acid were mixed with 242.3 grams of cysteine and then the acid solution was added to the cobalt carbonate-water mixture.

(4) The mixture was held at about 80° C. with continuous stirring until no more material would dissolve and the mixture was passed through a filter to remove the undissolved materials.

(5) The filtrate was dried at less than about 110° C. to obtain a cobalt amino acid chelate.

Chemical Analysis

Chemical analysis using atomic absorption spectrophotometer indicates the following metal contents of the exemplary novel enhanced chelates:

| Sample | Metal % |
|---|---|
| Sample I (iron chelate) | 17.2% Fe |
| Sample II (iron chelate) | 15.1% Fe |
| Sample III (calcium chelate) | 8.6% Ca |
| Sample IV (calcium chelate) | 8.3% Ca |
| Sample V (copper chelate) | 15.8% Cu |
| Sample VI (magnesium chelate) | 11.2% Mg |
| Sample VII (zinc chelate) | 16.0% Zn |
| Sample VIII (manganese chelate) | 9.0% Mn |
| Sample IX (cobalt chelate) | 14.8% Co |

The animal tests demonstrated that the iron chelates prepared as taught by this invention are better assimilated by animals as shown by the higher concentration of metals in the animals and the increased weight of the animal when compared with the control set.

Furthermore, amino acid chelated calcium prepared according to the invention disclosed herein forms no precipitate with additions of either sulfate or phosphate solutions at the normal application concentrations. Prior art preparations precipitate with both phosphate and sulfate solutions. It is common to mix other additives in animal feed. The invention eliminates the mixing problems when using phosphates of sulfates with chelated metal amino acids.

Likewise, the use of chelated metals prepared according to the invention, in all instances, show marked improvement in metal uptake and weight of growth over controls than the use of unchelated metal.

Further, experimentation has shown that the improved solubility and stability of the metal amino acid chelates produced by the process of the invention is unexpected. For example, according to prior formulations, a metal sulphate (e.g., cobalt sulphate) mixed with an amino acid results in a non-soluble compound which forms a milky aqueous solution (an emulsion). Adjustment of the pH of the aqueous solution does not convert the emulsion to a solution. Additionally, a metal salt reacted with an organic acid (e.g., ferrous sulfate plus citric acid) produces an insoluble material (i.e., ferrous citrate). But, mixing a metal sulphate with a solution composed of an amino acid and an organic acid (e.g., glycine plus citric acid) produces a material insoluble at low pH which can be converted to a clear solution by raising the pH above about 4.5.

Experimental results demonstrate that, metal amino acid chelates prepared accordingly to applicant's proprietary process, as first reduced to practice in U.S. Pat. No. 5,504,055; which is expressly incorporated herein by reference, are beneficial to animal growth. The following experiments have demonstrated these benefits:

Experiment 1

Sample I (Iron Chelate) was used in this experiment.

Forty sows were selected and randomly divided into 2 groups of 20 sows each. Sows in Group I received regular feed and sows in Group II received regular feed supplement with Sample I at 0.2% of total feed starting about 4 weeks before farrowing until 2 weeks after farrowing.

The number of baby pigs born, birth weight, number of baby pigs born alive and weight at weaning are shown in the following table:

|                              | Group I | Group II |
|------------------------------|---------|----------|
| Number of sows               | 20      | 20       |
| Total number of piglets born | 214     | 220      |
| Number of piglets born alive | 185     | 201      |
| Mortality, %                 | 13.6    | 8.6      |
| Average birth weight, kg.    | 1.29    | 1.34     |
| Number of piglets weaned     | 165     | 186      |
| Total weaning weight, kg.    | 877.80  | 1086.24  |
| Average weaning weight, kg.  | 5.32    | 5.84     |

The mortality of the piglets was reduced by feeding Sample I to the sows. Both total weaning weight and average weaning weight of piglets from sows receiving Sample I were higher than those receiving only the regular feed.

Experiment 2

Sample V (Copper Chelate) and Copper Sulfate were used in this experiment.

Sixty piglets with average age of 30 days were selected and randomly divided into 3 groups of 20 piglets each. During the 50 days experiment period the piglets of each group received the following feeding treatments:

Group I Regular Feed

Group II Regular Feed plus copper sulfate at 0.6 kg. per metric ton of feed.

Group III Regular feed plus Sample V at 1.0 kg. per metric ton of feed.

The weights of the piglets under study at the beginning and end of the experiment are shown in the following table:

|                            | Group I | Group II | Group III |
|----------------------------|---------|----------|-----------|
| Number of piglets          | 20      | 20       | 20        |
| Total beginning wt., kg.   | 124.9   | 130.2    | 128.1     |
| Average beginning wt., kg. | 6.3     | 6.5      | 6.4       |
| Total ending wt.,kg.       | 455.3   | 468.1    | 478.8     |
| Average ending wt., kg.    | 22.8    | 23.4     | 23.9      |
| Total wt. gained, kg.      | 330.4   | 337.9    | 350.7     |
| Average wt. gained, kg./pig| 16.5    | 16.9     | 17.5      |

The average weight gained for Group III piglets fed by Copper Chelate is greater than that for either Group I (control) or Group II (Copper Sulfate) piglets.

Experiment 3

Sample VII (Zinc Chelate) was used for this experiment.

Forty piglets with average age of 30 days were selected and randomly divided into 2 groups of 20 piglets each. During the 50 day experiment period the piglets of each group received the following feeding treatments:

Group I Regular feed

Group II Regular feed plus Sample VII at 1.0 kg. per metric ton of feed.

The weights of the piglets under study at the beginning and end of the experiment are shown in the following table:

|                             | Group I | Group II |
|-----------------------------|---------|----------|
| Number of piglets           | 20      | 20       |
| Total beginning wt., kg.    | 131.2   | 134.4    |
| Average beginning wt., kg.  | 6.6     | 6.7      |
| Total ending wt., kg.       | 477.1   | 496.6    |
| Average ending wt., kg.     | 23.9    | 24.8     |
| Total wt. gained, kg.       | 345.9   | 362.2    |
| Average wt. gained, kg./pig | 17.3    | 18.1     |

The average weight gained for Group II piglets fed Zinc Chelate is greater than that for Group I (control) piglets.

Experiment 4

Sample X was prepared by dissolving the following materials in 939.91 grams of water:
 a. 1.73 grams of Iron Chelate (Sample II)
 b. 5.82 grams of Calcium Chelate (Sample III)
 c. 0.70 grams of Copper Chelate (Sample V)
 d. 44.65 grams of Magnesium Chelate (Sample VI)
 e. 1.00 grams of Zinc Chelate (Sample VII)
 f. 6.11 grams of Manganese Chelate (Sample VIII)
 g. 0.08 grams of Cobalt Chelate (Sample IX)

All the materials were totally dissolved in water forming a dark brown liquid. The solution was analyzed to have the following quantities of minerals:

| Calcium (Ca)    | 500 ppm  |
| Cobalt (Co)     | 12 ppm   |
| Copper (Cu)     | 110 ppm  |
| Iron (Fe)       | 260 ppm  |
| Magnesium (Mg)  | 5000 ppm |
| Manganese (Mn)  | 550 ppm  |
| Zinc (Zn)       | 1600 ppm |

Sample X was used to conduct experiment described below:

Two chicken houses contained 25,000 white mountain broiler chicks each, were selected for this experiment. Both chicken houses were maintained in the same condition and the feeding programs were maintained identical except for the drinking water. In House I, regular drinking water was supplied and in House II, the drinking water received Sample X at a dosage of 4 milliliters per each liter of drinking water. The study was continued for 50 days.

The number of chicks at the beginning and end of the study, the total weight per house, and the total feed consumption are shown in the following table:

|                                  | House I | House II |
|----------------------------------|---------|----------|
| No. chicks, beginning            | 25,000  | 25,000   |
| No. chicks, end                  | 24,125  | 24,428   |
| Mortality, %                     | 3.5     | 2.3      |
| Total ending weight, kg.         | 45,354  | 47,636   |
| Average ending weight, kg/chick  | 1.88    | 1.95     |
| Total feed consumption, kg.      | 99,418  | 102,890  |
| Feed efficiency (feed/weight)    | 2.192   | 2.160    |

The mortality for House II which received Sample X is lower than for House I and the average chick weight for House II is greater than that for House I. The lower feed/weight for House II indicates that the chicks in House II had a better feed conversion. Further, while the weight per chick was increased about 3.7%, because mortality was decreased the total weight gain was over 5%.

Although the present invention has been described in considerable detail with reference to certain preferred versions and uses thereof, other versions and uses are possible. For example, the time and temperature of the various steps in the process can be varied. Additionally, the invention contemplates a broad range of organic acids, amino acids and metal salts as well as a range of ratios of the components metal amino acid chelate to increase weight gain and decrease mortality of animals. Other uses for the metal amino acid chelates of the invention include, but are not limited to, the delivery of metal ions to humans or as a reactant in chemical processes where the delivery of metal ions is required.

The process described by way of the present invention can therefore be used to facilitate and promote the growth of animals. Offered herein for consideration are applicant's teachings which have contributed both a way to prepare a chemical composition which has the unique capacity of increasing the uptake of desirable metallic ions in animals, and a means for increasing desired growth parameters in the same. Likewise, the chemical compositions produced under the processes of the present invention have not been shown in the prior art outside of applicant's own teachings. Therefore, the spirit and scope of the appended claims should not be limited to the description of the preferred versions contained herein.

What is claimed is:

1. A process to decrease still births and increase birth weight of babies born to non-human animals, comprising:
   preparing a metal containing process comprising the steps of:
   (a) deaerating water;
   (b) dissolving a metal salt in the deaerated water to produce a salt solution or forming a magnesium composition by adding metallic magnesium to the deaearated water;
   (c) mixing an organic acid selected from the group consisting of an organic hydroxy acid and malonic acid with an amino acid to provide an acid solution;
   (d) forming a chelate solution by adding the acid solution to the salt solution or said magnesium composition; and
   (e) adjusting the pH of the chelate solution to a range of from about 4.5 to about 8.5 by the addition of a base solution to yield an enhanced chelate;
   combining an effective amount of said enhanced chelate with animal feed and administering a resulting mixture to non-human animals prior to farrowing.

2. The process of claim 1 wherein the water is deaerated by boiling for at least about thirty minutes.

3. The process of claim 1 wherein the organic acid and the amino acid are mixed in a mole ratio from about 1:1 to about 1:10.

4. The process of claim 1 wherein the mole ratio of metal salt or metallic magnesium to acid in the acid solution is from about 1:1 to about 1:2.

5. The process of claim 1 wherein the mole ratio of free electrons on the metal ions to the —OOH groups on the organic acid and the amino acid is 2:1.

6. The process of claim 1 wherein the pH of the chelate is adjusted by adding a base selected from the group consisting of potassium hydroxide, sodium hydroxide and ammonium hydroxide.

7. The process of claim 1 wherein the metal salt has an anion selected from the group comprising acetates, oxides, sulfates, nitrates, chlorides, hydroxides, carbonates, phosphates and mixtures thereof and a cation selected from the group consisting of iron, cobalt, copper, zinc, chromium, magnesium, manganese, calcium, boron, molybdenum, nickel and mixtures thereof.

8. The process of claim 1 wherein the organic hydroxy acid is selected from the group consisting of citric acid, tartaric acid, lactic acid, gluconic acid and mixtures thereof.

9. The process of claim 1 wherein the amino acid is chosen from the group consisting of glycine, methionine, lysine, cysteine, glutamic acid, aspartic acid and mixtures thereof.

10. The process of claim 1 wherein the metal salt is selected from the group consisting of ferrous sulfate, ferrous carbonate, calcium carbonate, calcium chloride, cupric hydroxide, zinc oxide, manganous sulfate, and cobalt carbonate, the organic acid is selected from the group consisting of citric acid, glutamic acid, and malonic acid and the amino acid is selected from the group consisting of glycine, methionine, cysteine and lysine.

11. A process to decrease still births and increase birth weight of babies born to non-human animals comprising combining with animal feed an effective amount of at least one metal complex, said each at least one metal complex produced by blending magnesium or a metal salt, an amino acid and an organic acid selected from the group consisting of malonic acid and an organic hydroxy acid in deacrated water, the composition of mater being substantially soluble at a pH from about 4.5 to about 8.5, said complex having the structure:

$$R_2-CH-NH_2 \quad O-C=O$$
$$\diagdown \quad \diagup$$
$$M \quad (CH)_x$$
$$\diagup \quad \diagdown$$
$$O=C-O \quad O-A$$

Where M=a metal ion,
   x=0 or 1, and A=C=O or $CR_1R_3$
   $R_1$=a carbon chain derived from the organic hydroxy acid or malonic acid,
   $R_2$=H, or the carbon chain radical from the α-position of the amino acid, and
   $R_3$=—H or —COOH, and
feeding the combination of the animal feed with metal complex to pregnant non-human animals.

12. The process of claim 11 wherein the metal salt has an anion selected from the group consisting of sulfates, nitrates, chlorides, oxides, hydroxides, carbonates, phosphates, acetates, oxides and mixtures thereof and a cation selected from the group consisting of iron, cobalt, copper, zinc, magnesium, chromium, manganese, calcium, boron, molybdenum, nickel and mixtures thereof, the amino acid is selected from the group consisting of lysine, glycine, glutamic acid, aspartic acid, methionine, cysteine and mixtures thereof and the organic acid is selected from the group consisting of citric acid, lactic acid, malonic acid, tartaric acid, gluconic acid and mixtures thereof.

13. The process of claim 11 wherein the metal salt is selected from the group consisting of a water soluble salt of a sulfate, chloride, carbonate, oxide or hydroxide and mixtures thereof.

14. The process of claim 11 wherein the organic acid is selected from the group consisting of citric acid, glutamic acid and malonic acid.

15. The process of claim 11 wherein the amino acid is selected from the group consisting of glycine, methionine, cysteine and lysine.

16. The process of claim 15 wherein M is a metal ion selected from the group consisting of iron, cobalt, copper, zinc, magnesium, chromium, manganese, calcium, boron, molybdenum nickel and mixtures thereof.

17. The process of claim 15 wherein the amino acid is selected from the group consisting of glycine, methionine, lysine, cysteine, glutamic acid, aspartic acid and mixtures thereof.

18. The process of claim 15 wherein the organic acid is selected from the group consisting of citric acid, malonic acid, tartaric acid, lactic acid, gluconic acid and mixtures thereof.

19. The process of claim 15 wherein the metal ion is derived from a metal salt having an anion selected from the group consisting of sulfates, nitrates, chlorides, oxides, hydroxides, carbonates, phosphates, acetates, oxides and mixtures thereof and the metal ion is selected from the group consisting of iron, cobalt, copper, chromium, zinc, magnesium, manganese, calcium, boron, molybdenum, nickel and mixtures thereof and the organic acid is selected from the group consisting of citric acid, lactic acid, malonic acid, tartaric acid, gluconic acid and mixtures thereof.

20. The process of claim 11 which, when applied to pregnant pigs, results in an increased birth rate of piglets, said piglets having an increased birth weight and a decreased level of still births.

* * * * *